United States Patent
Chua et al.

(10) Patent No.: US 8,357,489 B2
(45) Date of Patent: Jan. 22, 2013

(54) METHODS FOR DETECTING HEPATOCELLULAR CARCINOMA

(75) Inventors: Mei-Sze Chua, Menlo Park, CA (US); Samuel So, Atherton, CA (US); Hongbo Sun, Fremont, CA (US); Dan-Hui Dorothy Yang, Sunnyvale, CA (US); Anya Tsalenko, Stanford, CA (US); Brian Jon Peter, Los Altos, CA (US)

(73) Assignees: The Board of Trustees of the Leland Stanford Junior University, Palo Alto, CA (US); Agilent Technologies, Inc., Santa Clara, CA (US)

( * ) Notice: Subject to any disclaimer, the term of this patent is extended or adjusted under 35 U.S.C. 154(b) by 268 days.

(21) Appl. No.: 12/618,376

(22) Filed: Nov. 13, 2009

(65) Prior Publication Data

US 2010/0120631 A1 May 13, 2010

Related U.S. Application Data

(60) Provisional application No. 61/114,132, filed on Nov. 13, 2008.

(51) Int. Cl.
*C12Q 1/68* (2006.01)
*G01N 33/53* (2006.01)

(52) U.S. Cl. .......................................... 435/6.1; 435/7.1
(58) Field of Classification Search ........................ None
See application file for complete search history.

(56) References Cited

PUBLICATIONS

Al-Wabel et al (Clinical Immunology and Immunopathology, 1995, 74(3): 231-235).*
Tockman et al (Cancer Res., 1992, 52:2711s-2718s).*
Rutkowski et al (Int J Cancer, 2002, 100: 463-471).*
Wong VW et al., "High serum interleukin-6 level predicts future hepatocellular carcinoma development in patients with chronic hepatitis B", Int J Cancer Jun. 15, 2009; 124(12):2766-70. PubMed PMID: 19267406.

* cited by examiner

*Primary Examiner* — Sean Aeder
(74) *Attorney, Agent, or Firm* — Andrea Blecken

(57) ABSTRACT

A method for evaluating hepatocellular carcinoma in a subject is provided. In certain embodiments, the method comprises: a) obtaining a hepatocellular carcinoma protein marker profile for a sample obtained from the subject; and b) comparing the protein marker profile to a control profile.

15 Claims, 6 Drawing Sheets

Fig. 1A

| Probe | t-test score p-value | Ratio fold change | t-test global p-value score | Order |
|---|---|---|---|---|
| Alpha-fetoprotein,500 | 0.003 | 2.40 | 0.011 | HBV+HCV < HCC |
| Total beta-Catenin,500 | 0.031 | 3.51 | 0.033 | HBV+HCV < HCC |
| M-CSF,500 | 0.036 | 1.46 | 0.044 | HBV+HCV < HCC |
| Total p21,500 | 0.050 | 1.49 | 0.048 | HBV+HCV < HCC |
| IL-1 ra,500 | 0.053 | 1.54 | 0.070 | HBV+HCV < HCC |
| Resistin,500 | 0.098 | 1.42 | 0.091 | HBV+HCV < HCC |
| L-Selectin,500 | 0.002 | -1.21 | 0.002 | HCC < HBV+HCV |
| IGFBP-6,500 | 0.014 | -1.15 | 0.019 | HCC < HBV+HCV |
| IL-6sR,500 | 0.020 | -1.10 | 0.021 | HCC < HBV+HCV |
| VCAM-1,500 | 0.046 | -1.07 | 0.044 | HCC < HBV+HCV |
| FGF-basic,500 | 0.074 | -1.59 | 0.091 | HCC < HBV+HCV |
| Fractalkine/CX3CL1,500 | 0.097 | -1.47 | 0.109 | HCC < HBV+HCV |

Fig. 2A

| Probe | t-test score p-value | Ratio fold change | t-test Global p-value score | Order |
|---|---|---|---|---|
| IL-1 ra,500 | 0.006 | 1.96 | 0.0027 | HBV+HCV; <HCC with AFP<20 |
| interferon-gamma,500 | 0.009 | 1.80 | 0.0064 | HBV+HCV; <HCC with AFP<20 |
| Total p21,500 | 0.019 | 1.67 | 0.0110 | HBV+HCV; <HCC with AFP<20 |
| Resistin,500 | 0.019 | 1.85 | 0.0131 | HBV+HCV; <HCC with AFP<20 |
| BRAK/CXCL14,500 | 0.022 | 1.65 | 0.0135 | HBV+HCV; <HCC with AFP<20 |
| Total beta-Catenin,500 | 0.026 | 3.91 | 0.0280 | HBV+HCV; <HCC with AFP<20 |
| M-CSF,500 | 0.055 | 1.51 | 0.0568 | HBV+HCV; <HCC with AFP<20 |
| TNF-beta,500 | 0.073 | 1.88 | 0.0642 | HBV+HCV; < HCC with AFP<20 |
| FGF-basic,500 | 0.021 | -3.61 | 0.0104 | HCC with AFP<20 <HBV+HCV |
| L-Selectin,500 | 0.039 | -1.19 | 0.0394 | HCC with AFP<20 <HBV+HCV |
| IL18,500 | 0.050 | -1.44 | 0.0432 | HCC with AFP<20 < HBV+HCV |
| IGFBP-6,500 | 0.078 | -1.16 | 0.0655 | HCC with AFP<20 <HBV+HCV |

Fig. 3A

| Probe | Ratio fold change | t-test global p-value score | t-test score p-value | Order |
|---|---|---|---|---|
| IGFBP-1,500 | 4.17 | 0 | 4.8E-06 | Normal < HCC |
| IL-8,500 | 2.97 | 1.52E-06 | 2.17E-06 | Normal < HCC |
| HGF,500 | 2.17 | 6.06E-06 | 4.44E-06 | Normal < HCC |
| ICAM-1,500 | 1.83 | 6.06E-06 | 5.84E-06 | Normal < HCC |
| IP-10,500 | 4.46 | 6.06E-06 | 3.76E-05 | Normal < HCC |
| TNFRSF11B,500 | 1.95 | 0.0006 | 1.01E-05 | Normal < HCC |
| TIMP2,500 | 1.38 | 0.0007 | 0.0011 | Normal < HCC |
| sTNF R1/TNFRSF1A,500 | 1.79 | 0.0047 | 0.0007 | Normal < HCC |
| MCP-1,500 | 1.44 | 0.0080 | 0.0073 | Normal < HCC |
| Alpha-fetoprotein,500 | 2.29 | 0.0086 | 0.0081 | Normal < HCC |
| IL-2sR alpha,500 | 1.47 | 0.0096 | 0.0098 | Normal < HCC |
| MMP-10,500 | 1.51 | 0.012 | 0.0111 | Normal < HCC |
| IL-6,500 | 1.61 | 0.012 | 0.0122 | Normal < HCC |
| IGFBP-4,500 | 1.54 | 0.021 | 0.0145 | Normal < HCC |
| IL18,500 | 1.55 | 0.055 | 0.0236 | Normal < HCC |
| MMP-9,500 | -1.67 | 0.0060 | 0.0046 | HCC < Normal |
| L-Selectin,500 | -1.15 | 0.0072 | 0.0059 | HCC < Normal |

METHODS FOR DETECTING HEPATOCELLULAR CARCINOMA

RELATED APPLICATION

This application claims priority and other benefits from U.S. Provisional Patent Application Ser. No. 61/114,132, filed Nov. 13, 2008, entitled 'Methods for Detecting Hepatocellular Carcinoma'. Its entire content is specifically incorporated herein by reference.

TECHNICAL FIELD OF THE INVENTION

The present invention relates generally to methods for the detection and diagnosis of hepatocellular carcinoma. More specifically, the present invention relates to methods for the detection and diagnosis of hepatocellular carcinoma through the quantitative and qualitative profiling of selected protein markers.

BACKGROUND

Hepatocellular carcinoma (HCC), the most common type of adult liver cancer, is the third leading cause of cancer deaths worldwide (Block T M et al. (2003), Oncogene 22, pp. 5093-5107). Many patients with HCC remain asymptomatic until the disease is in its advanced stages, resulting in ineffective treatment and poor prognosis; the majority of unresectable HCC patients die within one year. The clinical management of HCC can be expected to improve dramatically with improved screening tools to detect the carcinoma in the early stage.

The major risk factors of HCC are chronic infections with hepatitis B or hepatitis C virus (HBV or HCV, respectively). Chronic hepatitis can progress into cirrhosis (a noncancerous liver disease associated with fibrosis and abnormal nodules), which increases the risk of developing HCC. Patients with chronic hepatitis and/or cirrhosis, therefore, form a high risk population which would benefit from regular screening for HCC. Current screening tests for HCC are the measurement of alpha-fetoprotein (AFP) levels in the blood serum and the conduction of a hepatic ultrasound. Elevated serum AFP is, however, not a specific marker for HCC, since it is detected in a wide variety of non-hepatic malignancies and benign conditions, including acute and chronic hepatitis (McIntire KR et al. (1975), Cancer Res. 35, pp. 991-996; Liaw Y F (1986), Liver 6, pp. 133-137). Furthermore, 30-50% of HCC cases do not present with elevated serum AFP {Johnson P J (2001), Clin. Liver Dis. 5, pp. 145-159}. As a consequence, the AFP test can miss 50% of the positives due to its lack of sensitivity and specificity. A majority of HCC patients concomitantly suffers from cirrhosis. In those patients, the use of advanced imaging technology such as hepatic ultrasound is difficult and frequently non-conclusive.

Reliable non-invasive screening methods with improved sensitivity and specificity are critical and urgently needed for the accurate detection of HCC, particularly in high-risk subjects who exhibit symptoms of cirrhosis in the presence or absence of chronic hepatitis.

SUMMARY OF THE INVENTION

A method for evaluating hepatocellular carcinoma in a subject is provided. In certain embodiments, the method comprises: a) obtaining a hepatocellular carcinoma protein marker profile for a sample obtained from the subject; and b) comparing the protein marker profile to a control profile.

The subject methods may be employed to diagnose hepatocellular carcinoma, for example. In particular embodiments, the subject methods may be employed to differentiate between a subject having hepatocellular carcinoma and a subject having cirrhosis.

INCORPORATION BY REFERENCE

All publications, patent applications and patents mentioned in this specification are herein incorporated by reference to the same extent as if each individual publication or patent application was specifically and individually indicated to be incorporated by reference.

DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 1A and FIG. 1B show protein expression data for two sets of patients: HCC patients and patients having viral-induced cirrhosis.

FIG. 2A and FIG. 2B show protein expression data for two sets of patients: HCC patients having AFP levels of less than 20 μg/l and patients having viral-induced cirrhosis.

FIG. 3A and FIG. 3B show protein expression data for two sets of patients: HCC patients and patients having no clinical symptoms of HCC.

DEFINITIONS

Figure 1B:
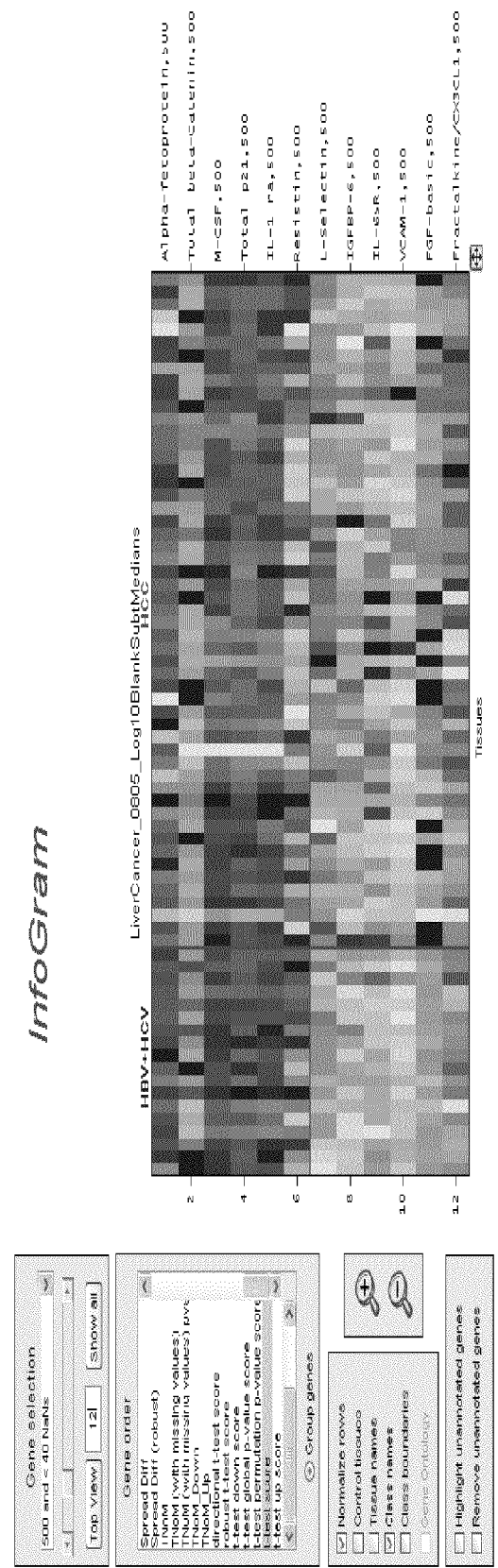

The term 'sample' as used herein relates to a material or mixture of materials, typically, although not necessarily, in fluid form, e.g., aqueous or in solvent, containing one or more components of interest. Samples may be derived from a variety of sources such as from food stuffs, environmental materials, a biological sample such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

A 'biopolymer' is a polymer of one or more types of repeating units, regardless of the source (e.g., biological (e.g., naturally-occurring, obtained from a cell-based recombinant expression system and the like or synthetic). Biopolymers may be found in biological systems and particularly include polypeptides and polynucleotides, including compounds containing amino acids, nucleotides, or a mixture thereof.

The terms 'polypeptide' and 'protein' are used interchangeably throughout the application and mean at least two covalently attached amino acids, which includes proteins, polypeptides, oligopeptides and peptides. A polypeptide may be made up of naturally occurring amino acids and peptide bonds, synthetic peptidomimetic structures, or a mixture thereof. Thus 'amino acid' or 'peptide residue', as used herein encompasses both naturally occurring and synthetic amino acids. For example, homo-phenylalanine, citrulline and noreleucine are considered amino acids for the purposes of the invention. 'Amino acid' also includes imino acid residues such as proline and hydroxyproline. The side chains may be in either the D- or the L-configuration. The term 'polypeptide' includes polypeptides in which the conventional backbone has been replaced with non-naturally occurring or synthetic backbones, and peptides in which one or more of the conventional amino acids have been replaced with one or more non-naturally occurring or synthetic amino acids.

The term 'fusion protein' or grammatical equivalents thereof references a protein composed of a plurality of polypeptide components, that while typically not attached in their native state, typically are joined by their respective amino and carboxyl termini through a peptide linkage to form a single continuous polypeptide. Fusion proteins may be a combination of two, three or even four or more different proteins. The term 'polypeptide' includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, and the like.

In general, biopolymers, e.g., polypeptides or polynucleotides, may be of any length, e.g., greater than 2 monomers, greater than 4 monomers, greater than about 10 monomers, greater than about 20 monomers, greater than about 50 monomers, greater than about 100 monomers, greater than about 300 monomers, usually up to about 500, 1000 or 10,000 or more monomers in length. 'Peptides' and 'oligonucleotides' are generally greater than 2 monomers, greater than 4 monomers, greater than about 10 monomers, greater than about 20 monomers, usually up to about 10, 20, 30, 40, 50 or 100 monomers in length. In certain embodiments, peptides and oligonucleotides are between 5 and 30 amino acids in length.

The term 'capture agent' refers to an agent that binds a target molecule through an interaction that is sufficient to permit the agent to bind and concentrate the target molecule from a homogeneous mixture of different molecules. The binding interaction is typically mediated by an affinity region of the capture agent. Typical capture agents include any moiety that can specifically bind to a target molecule. In certain embodiments, a polypeptide, e.g., an antibody protein, may be employed. Capture agents usually 'specifically bind' a target molecule. Accordingly, the term 'capture agent' refers to a molecule or a multi-molecular complex which can specifically bind a target molecule, e.g., a phosphorylated polypeptide, with a dissociation constant ($K_D$) of less than about $10^{-6}$ M (e.g., less than about $10^{-7}$M, less than about $10^{-8}$M, less than about $10^{-9}$M, less than about $10^{-10}$ M, less than about $10^{-11}$ M, less than about $10^{-12}$ M, to about usually up to about $10^{-16}$ M) without significantly binding to other molecules.

The term 'specific binding' refers to the ability of a capture agent to preferentially bind to a particular target molecule that is present in a homogeneous mixture of different target molecule. In certain embodiments, a specific binding interaction will discriminate between desirable and undesirable target molecules in a sample, typically more than about 10 to 100-fold or more (e.g., more than about 1000- or 10,000-fold).

The term 'capture agent/target complex' is a complex that results from the specific binding of a capture agent with a target, i.e., a 'binding partner pair'. A capture agent and a target for the capture agent will usually specifically bind to each other under 'conditions suitable for specific binding', where such conditions are those conditions (in terms of salt concentration, pH, detergent, protein concentration, temperature, etc.) which allow for binding to occur between capture agents and targets to bind in solution. Such conditions, particularly with respect to proteins and antibodies, include those described in Harlow and Lane (Antibodies: A Laboratory Manual Cold Spring Harbor Laboratory, Cold Spring Harbor, N.Y. (1989)) and Ausubel, et al (Short Protocols in Molecular Biology, 5th ed., Wiley & Sons, 2002).

As used herein, 'binding partners' and equivalents thereof refer to pairs of molecules that can be found in a capture agent/target complex, i.e., exhibit specific binding with each other.

A 'surface-bound capture agent' refers to a capture agent that is immobilized on a surface of a substrate. In certain embodiments, the capture agent employed herein may be present on a surface of the same support, e.g., in the form of an array.

The term 'pre-determined' refers to an element whose identity is known prior to its use. An element may be known by name, sequence, molecular weight, its function, or any other attribute or identifier. In some embodiments, the term 'polypeptide of interest', i.e., a known polypeptide that is of interest, is used synonymously with the term 'pre-determined polypeptide'.

The term 'antibody protein' is used herein to refer to a capture agent that has at least an epitope binding domain of an antibody. These terms are well understood by those in the field, and refer to a protein containing one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions. Several types of antibodies, including antibody isotypes, monoclonal antibodies and antigen-binding fragments thereof (e.g., Fab, Fv, scFv, and Fd fragments, chimeric antibodies, humanized antibodies, single-chain antibodies) are known and described in further detail in, e.g., William Paul, Fundamental Immunology, $4^{th}$ edition (1999), Lippincott Williams & Wilkins.

An 'array' includes any one-dimensional, two-dimensional, substantially two-dimensional as well as a three-dimensional arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the arrays are arrays of polymeric binding agents, where the polymeric binding agents may be any of: polypeptides, proteins, nucleic acids, polysaccharides, synthetic mimetics of such biopolymeric binding agents, etc. In certain embodiments, the arrays are arrays of antibodies against the markers described below.

Any given substrate may carry one, two, four or more arrays disposed on a front surface of the substrate. Depending upon the intended use, any or all of the arrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either precursor units (such as amino acid or nucleotide monomers) in the case of in situ fabrication, or the previously obtained polymer. Such methods are described in detail in, for example, U.S. Pat. No. 6,242,266; U.S. Pat. No. 6,232,072; U.S. Pat. No. 6,180,351; U.S. Pat. No. 6,171,797; U.S. Pat. No. 6,323,043; U.S. Pat. No. 6,242,266 and other references. Other drop deposition methods can be used for fabrication, as previously described herein. Also, instead of drop deposition methods, photolithographic array fabrication methods may be used. Interfeature areas need not be present particularly when the arrays are made by photolithographic methods.

An array is 'addressable' when it has multiple regions of different moieties (e.g., different polynucleotide sequences) such that a region (i.e., a 'feature' or 'spot' of the array) at a particular predetermined location (i.e., an 'address') on the array will detect a particular target or class of targets (although a feature may incidentally detect non-targets of that feature). Array features are typically, but need not be, separated by intervening spaces. In the case of an array, the 'target' will be referenced as a moiety in a mobile phase (typically fluid), to be detected by probes ('target probes') which are bound to the substrate at the various regions. However, either of the 'target' or 'target probe' may be the one which is to be evaluated by the other (thus, either one could be an unknown mixture of polynucleotides to be evaluated by binding with the other). A 'scan region' refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An 'array layout' refers to one or more characteristics of the features, such as feature positioning on the substrate, one or more feature dimensions, and an indication of a moiety at a given location. 'Hybridizing' and 'binding', with respect to polynucleotides, are used interchangeably.

The term 'mixture', as used herein, refers to a combination of elements, e.g., proteins, that are interspersed and not in any particular order. A mixture is homogeneous and not spatially separated into its different constituents. Examples of mixtures of elements include a number of different elements that are dissolved in the same aqueous solution, or a number of different elements attached to a solid support at random or in no particular order in which the different elements are not specifically distinct. In other words, a mixture is not addressable. To be specific, an array of polypeptides, as is commonly known in the art, is not a mixture of polypeptides because the species of polypeptide on an array are spatially distinct and addressable.

'Isolated' or 'purified' generally refers to isolation of a substance (compound, polynucleotide, protein, polypeptide, polypeptide composition) such that the substance comprises a significant percent (e.g., greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term 'assessing' includes any form of measurement, and includes determining if an element is present or not. The terms 'determining', 'measuring', 'evaluating', 'assessing' and 'assaying' are used interchangeably and may include quantitative and/or qualitative determinations. Assessing may be relative or absolute. 'Assessing the presence of' includes determining the amount of something present, and/or determining whether it is present or absent.

The term 'using' has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

If one composition is 'bound' to another composition, the compositions do not have to be in direct contact with each other. In other words, bonding may be direct or indirect, and, as such, if two compositions (e.g., a substrate and a polypeptide) are bound to each other, there may be at least one other composition (e.g., another layer) between to those compositions. Binding between any two compositions described herein may be covalent or non-covalent. The terms 'bound' and 'linked' are used interchangeably herein.

The term 'hepatocellular carcinoma' (or 'HCC' for short) refers to a malignant tumor of hepatocellular origin that may develop in patients with risk factors that include alcohol abuse, viral hepatitis, and metabolic liver disease. HCC is a type of liver cancer. HCC can undergo hemorrhage and necrosis because of a lack of fibrous stroma. Vascular invasion, particularly of the portal system, is common. Aggressive HCC can cause hepatic rupture and hemoperitoneum.

Other definitions of terms appear throughout the specification.

DETAILED DESCRIPTION

A method for evaluating hepatocellular carcinoma in a subject is provided. In certain embodiments, the method comprises: a) obtaining a hepatocellular carcinoma protein marker profile for a sample obtained from the subject; and b) comparing the protein marker profile to a control profile.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

Hepatocellular Carcinoma Protein Markers

Many embodiments of the instant methods include obtaining an hepatocellular carcinoma (HCC) protein marker profile for a sample, where an HCC protein marker profile is a profile of least three markers that, together, provide a reliable evaluation of HCC. Some embodiments of the instant methods include obtaining an hepatocellular carcinoma (HCC) protein marker profile for a sample, where an HCC protein marker profile is a profile of at least one marker to reliably evaluate HCC. Some embodiments of the instant methods include obtaining an hepatocellular carcinoma (HCC) protein marker profile for a sample, where an HCC protein marker profile is a profile of at least two markers to reliably evaluate HCC. In other words, to evaluate whether a subject has HCC, the presence of one or more HCC protein markers in a sample is assessed to produce a profile, and that profile is compared to a control profile to evaluate HCC. A statistically significant match with a positive control profile or a statistically significant difference from a negative control profile indicates that the subject has HCC. The HCC protein marker profile may be employed to distinguish subjects having HCC from subjects having cirrhosis.

While a wide range of proteins may be employed as HCC protein markers, the HCC protein markers employed in many embodiments of the instant methods include proteins selected from the group consisting of: β-Catenin, M-CSF, Total p21, IL-1-ra, Resistin, L-Selectin, IGFBP-6, IL-6sR, VCAM-1, FGF-basic, Fractalkine/CX3CL1, Interferon-gamma, BRAK/CXCL14, TNF-beta, IL18, IGFBP-1, IL8, HGF, ICAM-1, IP-10, TNFRSF11B, TIMP2, sTNF R1/TNFRSF1A, MCP-1, IL-2sR alpha, MMP10, IL-6, and IGFBP-4. As such, in certain embodiments, the instant methods include: obtaining an HCC protein marker profile that includes quantitative data for at least three protein markers (e.g., 3, 4, 5, 6, 7, 8, 9, 10, 11, 12, 13, 14, 15, 16, 17, 18, 19, 20, 21, 22, 23, 24, 25, 26, 27 or all of the protein markers) selected from the group consisting of: β-Catenin, M-CSF, Total p21, IL-1-ra, Resistin, L-Selectin, IGFBP-6, IL-6sR, VCAM-1, FGF-basic, Fractalkine/CX3CL1, Interferon-gamma, BRAK/CXCL14, TNF-beta, IL18, IGFBP-1, IL8, HGF, ICAM-1, IP-10, TNFRSF11B, TIMP2, sTNF R1/TNFRSF1A, MCP-1, IL-2sR alpha, MMP10, IL-6, and IGFBP-4, and comparing the profile with a control profile. In certain embodiments, the instant methods include: obtaining an HCC protein marker profile that includes quantitative data for at least one protein marker selected from the group consisting of: M-CSF, IL8 and MMP10, and comparing the profile with a control profile. In certain embodiments, the instant methods include: obtaining an HCC protein marker profile that includes quantitative data for at least two protein markers selected from the group consisting of: M-CSF, IL8 and MMP10, and comparing the profile with a control profile. In certain embodiments, the method may further include evaluating alpha fetoprotein levels. Each of these proteins is discussed in greater detail below.

β-Catenin (CTNNB1) is an 88 kD adherens junction protein. β-Catenin is thought to be critical for the establishment and maintenance of epithelial layers, such as those lining organ surfaces. β-Catenin may also mediate adhesion between cells, communicate a signal that neighboring cells are present, and anchor the actin cytoskeleton. β-Catenin is further described in record 116806 of NCBI's OMIM database.

M-CSF (mononuclear phagocyte colony-stimulating factor, also know as CSF-1) is a disulfide-bonded glycoprotein dimer with a MW of 70 kDa normally synthesized by mesenchymal cells. The compound stimulates the survival, proliferation, and differentiation of hematopoietic cells of the monocyte-macrophage serie, and binds to a specific high affinity receptor. M-CSF is further described in record 120420 of NCBI's OMIM database.

Total p21 is also known as cyclin-dependent kinase inhibitor-1A (CDKN1A), or CDK-interacting protein 1 (CIP1). p21 inhibits cyclin-kinase activity, and is regulated at the transcriptional level by the p53 tumor suppressor, and probably serves as the effector of p53 cell cycle control. p21 is further described in record 116899 of NCBI's OMIM database.

IL-1 ra (interleukin-1 receptor antagonist, also known as IL1RN) shows partial homology to IL-1 alpha and IL-1 beta, and inhibits the binding of IL1-alpha and IL1-beta to IL1 receptors. IL-1 ra blocks the inflammatory response induced by IL-1 in vivo and in vitro. IL-1 ra is further described in record 147679 of NCBI's OMIM database.

Resistin is a hormone secreted by adipose tissue. It is also known as 'serine/cysteine-rich adipocyte-Specific Secretory Factor' (ADSF or FIZZ3). The length of the resistin prepeptide in human is 108 amino acids (in the mouse and rat it's 114 aa); the molecular weight of Resistin is about 12.5 kDa. Resistin is further described in record 605565 of NCBI's OMIM database.

L-Selectin (also known as lymphocyte adhesion molecule 1) is a cell surface component that is a member of a family of adhesion proteins. The molecule is composed of multiple domains: 1 homologous to lectins, 1 to epidermal growth factor, and 2 to the consensus repeat units found in C3/C4 binding proteins. L-selectin is further described in record 153240 of NCBI's OMIM database.

IGFBP-6, or insulin-like growth factor binding protein-6, is a protein that binds to insulin-like growth factors in extracellular fluids with high affinity. IGF-binding proteins prolong the half-life of the IGFs and have been shown to either inhibit or stimulate the growth promoting effects of the IGFs on cells culture. The human IGFBP6 gene codes for a 216-amino acid protein with a calculated molecular weight of 22,847. IGFBP-6 has the highest affinity for IGF, is expressed in fibroblasts and prostatic and ovarian cells, and is found in CSF and serum. IGFBP-6 is further described in record 146735 of NCBI's OMIM database.

IL-6sR is the soluble form of the interleukin-6 receptor that is found in blood serum. IL-6 is a multifunctional cytokine that is essential to the regulation of the immune response, hematopoiesis, and acute-phase reactions. The gene that encodes the IL-6 receptor encodes a protein consisting of 468 amino acids, including a signal peptide of about 19 amino acids and a domain of about 90 amino acids that is similar to a domain in the immunoglobulin superfamily. The cytoplasmic domain of about 82 amino acids lacks a tyrosine/kinase domain, unlike other growth factor receptors. IL-6sR is further described in record 147880 of NCBI's OMIM database.

VCAM-1 (Vascular cell adhesion molecule-1) is a cell surface glycoprotein expressed by cytokine-activated endothelium and mediates the adhesion of monocytes and lymphocytes. In inflammatory conditions and in cardiac allografts undergoing rejection, VCAM1 is upregulated in endothelium of postcapillary venules. VCAM-1 is further described in record 192225 of NCBI's OMIM database.

FGF-basic (or bFGF, FGF2) is a single-chain polypeptide growth factor that plays a significant role in the process of wound healing and is a potent inducer of angiogenesis. Several different forms of the human protein exist ranging from 18-24 kDa in size due to the use of alternative start sites within the fgf-2 gene. It has a 55 percent amino acid residue identity to FGF-1 and has potent heparin-binding activity. The growth factor is an extremely potent inducer of DNA synthesis in a variety of cell types from mesoderm and neuroectoderm lineages. It was originally named basic fibroblast growth factor based upon its chemical properties and to distinguish it from acidic fibroblast growth factor. FGF-basic is further described in record 134920 of NCBI's OMIM database.

Fractalkine/CX3CL1 is a shed 95-kD glycoprotein. Soluble fractalkine is a cytokine that has potent chemoattractant activity for T cells and monocytes. Fractalkine is further described in record 601880 of NCBI's OMIM database.

Interferon-gamma (IFN-gamma) is produced by lymphocytes activated by specific antigens or mitogens. IFN-gamma shows antiviral activity and has important immunoregulatory functions. It is a potent activator of microphages and had antiproliferative effects on transformed cells. It can potentiate the antiviral and antitumor effects of the type I interferons. Interferon-gamma is further described in record 147570 of NCBI's OMIM database.

BRAK/CXCL14 (or breast and kidney expressed chemokine) is proposed to be involved in the homeostasis of monocyte-derived macrophages rather than in inflammation, and thought to be a potent inhibitor of angiogenesis and a chemotactic factor for immature dendritic cells. BRAK is a CXC chemokine, and is further described in record 604186 of NCBI's OMIM database.

TNF-beta (Tumor Necrosis Factor-beta or lymphotixin-alpha) is a potent lymphoid factor, which exerts cytotoxic effects on a wide range of tumor cells and certain other target cells. Human TNF-beta is an 18.6 kDa protein containing 172 amino acid residues. TNF-beta is a homotrimer and binds TNFR-1 and TNFR-2. Due to glycosylation, TNF-beta has an approximate molecular weight of 19.3 kDa based on SDS-PAGE gel and mass spectrometry. TNF-beta is further described in record 153440 of NCBI's OMIM database.

IL18, otherwise known as interferon-gamma-inducing factor (IGIF), augments natural killer (NK) cell activity in spleen cells. The IL18 gene encodes a precursor protein of 192 amino acids and a mature protein of 157 amino acids. IL18 is further described in record 600953 of NCBI's OMIM database.

IGFBP-1 (IGF-binding protein I) binds IGF I and IGF II with high affinity to form a complex, and that complex circulates in plasma. IGFBP1 is synthesized in liver, secretory endometrium, and decidua. IGFBP-1 is further described in record 146730 of NCBI's OMIM database.

IL8 (Interleukin-8), also called neutrophil-activating peptide-1 or SCYB8, is a tissue-derived peptide secreted by several types of cells in response to inflammatory stimuli. IL8 is one of a family of 13 human CXC chemokines. These small basic heparan-binding proteins are proinflammatory and primarily mediate the activation and migration of neutrophils into tissue from peripheral blood. Human IL8 is further described in record 146930 of NCBI's OMIM database.

HGF (hepatocyte growth factor) is a growth factor with strong mitogenic activity on hepatocytes and primary epithelial cells through interaction with its receptor (c-met). HGF has multifunctional activities that regulate cell growth and motility. Purified HGF from a patient's plasma showed that it has multiple forms with molecular weights between 76,000 and 92,000. HGF consists of 2 chains, heavy and light, with molecular weights of 54,000-65,000 and 31,500-34,500, respectively. These chains are linked together by disulfide bonds. Human HGF is further described in record 142409 of NCBI's OMIM database.

ICAM-1 (intercellular adhesion molecule, 1; CD54) is expressed on endothelial cells and cells of the immune system. ICAM1 binds to integrins of type CD11a/CD18, or CD11b/CD18 and is also exploited by Rhinovirus as a receptor. ICAM is expressed on vascular endothelium and leukocytes, up-regulated by cytokines. Human ICAM1 is further described in record 147840 of NCBI's OMIM database.

IP-10, otherwise known as CXCL10, is a member of the alpha-chemokine family and inhibits bone marrow colony formation, has antitumor activity in vivo, is a chemoattractant for human monocytes and T cells, and promotes T cell adhesion to endothelial cells. It has been reported that IP-10 is a potent inhibitor of angiogenesis in vivo, and proposed that IP10 may participate in the regulation of angiogenesis during inflammation and tumorigenesis. Human IP-10 is further described in record 147310 of NCBI's OMIM database.

TNFRSF11B (tumor necrosis factor receptor superfamily, member 11b) otherwise known as osteoprotegerin, neutralizes RANKL function in osteoclastogenesis. TNFRSF11B inhibits the activation of osteoclasts and promotes osteoclast apoptosis in vitro. It is thought that TNFRSF11B plays a role in bone homeostasis and in arterial calcification. TNFRSF11B contains a small cytoplasmic tail with two DEATH domains that exist in a secreted form TNFRSF11B. Human TNFRSF11B is further described in record 602643 of NCBI's OMIM database.

TIMP2 (tissue inhibitor of metalloproteinase 2) is a member of the TIMP family. The proteins of this family are natural inhibitors of the matrix metalloproteinases, a group of peptidases involved in degradation of the extracellular matrix. In addition to an inhibitory role against metalloproteinases, the protein has a unique role among TIMP family members in its ability to directly suppress the proliferation of endothelial cells. As a result, the protein may be critical to the maintenance of tissue homeostasis by suppressing the proliferation of quiescent tissues in response to angiogenic factors, and by inhibiting protease activity in tissues undergoing remodelling of the extracellular matrix. Human TIMP2 is further described in record 188825 of NCBI's OMIM database.

sTNF R1/TNFRSF1A (Tumor Necrosis Factor receptor superfamily, member 1A) is a member of the TNF-receptor superfamily. This protein is one of the major receptors for the tumor necrosis factor-alpha. This receptor can activate NF-kappaB, mediate apoptosis, and function as a regulator of inflammation. Antiapoptotic protein BCL2-associated athanogene 4 (BAG4/SODD) and adaptor proteins TRADD and TRAF2 have been shown to interact with this receptor, and thus play regulatory roles in the signal transduction mediated by the receptor. Human sTNF R1/TNFRSF1A is further described in record 191190 of NCBI's OMIM database.

MCP-1 (monocyte chemotactic protein-1) is a member of the small inducible gene (SIG) family, and plays a role in the recruitment of monocytes to sites of injury and infection. Human MCP-1 is approximately 76 amino acid residues in length and further described in record 158105 of NCBI's OMIM database.

IL-2sR alpha, also known as Tac antigen and as CD25, is a soluble form of the interleukin-2 receptor alpha, where IL-2 is a powerful immunoregulatory lymphokine that is produced by lectin- or antigen-activated T cells. IL-2 is produced not only by mature T lymphocytes on stimulation but also constitutively by certain T-cell lymphoma cell lines. IL-2sR alpha is further described in record 147730 of NCBI's OMIM database.

MMP-10 (matrix metalloproteinase 10), also known as stromelysin II, is a metalloproteinase related to collagenase whose substrates include proteoglycans and fibronectin, but not type I collagen. Proteins of the matrix metalloproteinase family are involved in the breakdown of extracellular matrix in normal physiological processes, such as embryonic development, reproduction, and tissue remodeling as well as in disease processes such as cancer and cardiovascular disease. MMP-10 expression has been observed in carcinoma cells of the human head, neck and lung carcinomas. MMP-10 is further described in record 185260 of NCBI's OMIM database.

IL-6 (Interleukin-6) also referred to as B-cell stimulatory factor-2 (BSF-2) and interferon beta-2, is a cytokine involved in a wide variety of biological functions. It plays an essential role in the final differentiation of B-cells into immunoglobulin-secreting cells, as well as inducing myeloma/plasmacytoma growth, nerve cell differentiation and, in hepatocytes, acute phase reactants. Cytokines of the IL6 family are glycoproteins of about 170 to 180 amino acid residues that contains four conserved cysteine residues involved in two disulphide bonds. Human IL-6 is further described in record 147620 of NCBI's OMIM database.

IGFBP-4 (Insulin-like Growth Factor-binding protein 4) is a member of the insulin-like growth factor binding protein (IGFBP) family and has an IGFBP domain and a thyroglobulin type-I domain. The protein binds both insulin-like growth factors (IGFs) I and II and circulates in the plasma in both glycosylated and non-glycosylated forms. Binding of this protein prolongs the half-life of the IGFs and alters their interaction with cell surface receptors. IGFBP4 is involved in the systemic and local regulation of IGF activity. Human IGFBP4 is further described in record 146733 of NCBI's OMIM database.

Other exemplary proteins that may be employed in the subject methods may be listed in the figures.

In a particular embodiment, the hepatocellular carcinoma protein marker profile may include quantitative data for at least three protein markers (e.g., 3, 4, 5, 6, 7, 8, 9, 10 or 11 protein markers) selected from the group consisting of: total beta-Catenin, M-CSF, Total p21, IL-1 ra, Resistin, L-Selectin, IGFBP-6, IL-6sR, VCAM-1, FGF-basic and Fractalkine/CX3CL1. In another embodiment, the hepatocellular carcinoma protein marker profile may include quantitative data for at least one protein marker selected from the group consisting of: M-CSF, IL8 and MMP10. In yet another embodiment, the hepatocellular carcinoma protein marker profile may include quantitative data for at least two protein markers selected from the group consisting of: M-CSF, IL8 and MMP10. In these embodiments, the control profile may be obtained from subjects having cirrhosis or subjects having hepatitis infection, e.g., HCV or HBV infection.

In another embodiment, the subject being tested has alpha-fetoprotein serum levels of less than 20 µg/l. In this embodiment, the hepatocellular carcinoma protein marker profile may include quantitative data for at least three protein markers (e.g., 3, 4, 5, 6, 7, 8, 9, 10, 11 or 12 protein markers) selected from the group consisting of: IL-1 ra, interferon-gamma, Total p21, Resistin, BRAK/CXCL14, Total beta-Catenin, M-CSF, TNF-beta, FGF-basic, L-Selectin, IL18, and IGFBP-6. In another embodiment, the hepatocellular carcinoma protein marker profile may include quantitative data for at least one protein marker selected from the group consisting of: M-CSF, IL8 and MMP10. In yet another embodiment, the hepatocellular carcinoma protein marker profile may include quantitative data for at least two protein markers selected from the group consisting of: M-CSF, IL8 and MMP10. In these embodiments, the control profile may be obtained from subjects having cirrhosis or subjects having hepatitis infection, e.g., HCV or HBV infection. These embodiments provide a method for detecting HCC in subjects that may be otherwise diagnosed as not having HCC if an AFP-based assay were employed.

In a further embodiment, the hepatocellular carcinoma protein marker profile may include quantitative data for at least three protein markers (e.g., 3, 4, 5, 6, 7, 8, 9, 10, 11, 12, 13, 14, 15 or 16 protein markers) selected from the group consisting of: IGFBP-1, IL-8, HGF, ICAM-1, IP-10, TNFRSF11B, TIMP2, sTNF R1/TNFRSF1A, MCP-1, IL-2sR alpha, MMP-10, IL-6, IGFBP-4, IL18, MMP-9 and L-Selectin. In another embodiment, the hepatocellular carcinoma protein marker profile may include quantitative data for at least one protein marker selected from the group consisting of: M-CSF, IL8 and MMP10. In yet another embodiment, the hepatocellular carcinoma protein marker profile may include quantitative data for at least two protein markers selected from the group consisting of: M-CSF, IL8 and MMP10. In these embodiments, the control profile may be obtained from normal subjects, e.g., subjects that have no clinical symptoms of liver disease.

Methods of Detection

Various systems and methods may be employed in obtaining a hepatocellular carcinoma protein marker profile for a sample. In one embodiment, a sample (e.g., whole blood, plasma or serum) is assayed for the presence of protein markers. In other words, a blood sample may be drawn, and a blood product, e.g., whole blood, plasma or serum, may be tested. The HCC protein markers may be detected using specific capture agents, e.g., antibody proteins, for the HCC marker proteins. In certain embodiments, the method employed may provide a quantitative evaluation of the presence of at least three of the above-described HCC protein markers in the sample. In other embodiments, the method employed may provide a quantitative evaluation of the presence of at least one protein marker selected from the group consisting of: M-CSF, IL8 and MMP10. In other embodiments, the method employed may provide a quantitative evaluation of the presence of at least two protein markers selected from the group consisting of: M-CSF, IL8 and MMP10.

Various detection platforms may be employed in such methods, including antibody arrays, labeled bead assays, ELISA and RIA formats, binding of labeled antibodies in suspension/solution and detection by flow cytometry, mass spectroscopy, and the like. A variety of different assays can be utilized to quantitate HCC marker protein levels, including both methods that detect gene transcript and protein levels. Many of such methods are known to one of skill in the art, including ELISA, protein arrays, eTag system, bead based system, antibody-based systems, nucleic acid and/or small molecule systems, tag or other array based systems. Examples of such methods are set forth in the art, including, inter alia, chip-based capillary electrophoresis: Colyer et al. (1997) J Chromatogr A. 781(1-2):271-6; mass spectroscopy: Petricoin et al. (2002) Lancet 359: 572-77; eTag systems: Chan-Hui et al. (2004) Clinical Immunology 111:162-174; microparticle-enhanced nephelometric immunoassay: Montagne et al. (1992) Eur J Clin Chem Clin Biochem. 30(4):217-22; and the like, each of which are herein incorporated by reference.

In certain embodiments, detection may utilize a panel of capture agents, e.g., a panel of antibodies in an array format. In one exemplary embodiment, a sample, e.g., plasma or serum sample, may be applied to a specific binding agent or panel of specific binding agents, to quantitatively determine the presence of the marker or markers of interest.

A profile (i.e., a dataset containing quantitative information on the expression of the marker protein or proteins in sample) can be generated from a biological sample using any convenient protocol. Assays for expression of the subject sequences may be based on the functional or antigenic characteristics of the protein. Various immunoassays designed to quantitate proteins may be employed. One method for diagnosis depends on the in vitro detection of binding between antibodies and the marker protein(s) in the sample. Evaluating the amount of the target protein in a sample or fraction thereof may be accomplished by a variety of specific assays.

For example, a conventional sandwich type assay may be used in an array, ELISA, RIA, and the like format. A sandwich assay may first attach specific antibodies to an insoluble surface or support. The particular manner of binding is not crucial, as long as it is compatible with the reagents and overall methods of the invention. The reagents may be bound to the solid surfaces covalently or non-covalently.

An insoluble support may be any composition to which polypeptides can be bound, which is readily separated from soluble material, and which is otherwise compatible with the overall method. The surface of such a support may be solid or porous and of any convenient shape. Examples of suitable insoluble supports to which the receptor is bound include beads, e.g. magnetic beads, membranes, slides and microtiter plates. These substrates are typically made of glass, plastic (e.g. polystyrene), polysaccharides, nylon or nitrocellulose or other chemically modified surface. Microtiter plates are convenient because a large number of assays can be carried out simultaneously, using small amounts of reagents and samples.

Patient samples may be added to separately assayable supports (for example, separate wells of a microtiter plate), or to the surface of an array, containing capture agents, e.g., antibodies. In one embodiment, a series of standards, containing known concentrations of the test protein is assayed in parallel with the samples or aliquots thereof to serve as controls. In certain embodiments, each sample and standard may be added to multiple wells so that mean values can be obtained for each. The incubation time should be sufficient for binding, generally, from about 0.1 to 3 hr is sufficient, though longer incubations (such as overnight, or 24 hours) may also be used. After incubation, the insoluble support is generally washed of non-bound components. Generally, a diluted non-ionic detergent medium at an appropriate pH, generally 7-8, is used as a wash medium. From one to six washes may be employed, with sufficient volume to thoroughly wash non-specifically bound proteins present in the sample.

After washing, a solution containing a second antibody is applied. The antibody will bind to one of the proteins of interest with sufficient specificity such that it can be distinguished from other components present. The second antibodies may be labeled to facilitate direct or indirect quantification of binding. Examples of labels that permit direct measurement of second receptor binding include radiolabels, such as $^3$H or $^{125}$I, fluorescers, dyes, beads, chemiluminescers, colloidal particles, and the like. Examples of labels that permit indirect measurement of binding include haptens, small molecules such as biotin, digoxigenin and the like, or enzymes where the substrate may provide for a colored or fluorescent product. In one embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material, leaving the specific complex formed between the target protein and the specific binding member. The signal produced by the bound conjugate is detected by conventional means. Where an enzyme conjugate is used, an appropriate enzyme substrate is provided so a detectable product is formed. Where an indirect label such as biotin is used, a labeled detection molecule such as fluorescently-labeled streptavidin may be used. Other suitable methods of detection are well known to those skilled in the art.

Alternatively, detection may utilize direct staining of cells or a sample bound to a solid support, performed in accordance with conventional methods, using antibodies or other specific binding members that specifically bind to the HCC marker or markers. The antibodies or other specific binding members of interest, e.g., receptor ligands, are added to a cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a secondary antibody or reagent is used to amplify the signal. Such reagents are known in the art. For example, the secondary antibody may be conjugated to biotin, with horseradish peroxidase-conjugated or fluorophor-conjugated avidin added to generate signal. Final detection uses a substrate that undergoes a color change in the presence of the peroxidase or direct fluorescence readout. The absence or presence of antibody binding may be determined by various methods, including flow cytometry of dissociated cells, microscopy, radiography, scintillation counting, and the like.

Other immunoassays are known in the art and may find use as diagnostics. For example, Ouchterlony plates provide a simple determination of antibody binding. Western blots may be performed on protein gels or protein spots on filters, using a detection system specific for the HCC associated polypeptide as desired, conveniently using a labeling method as described for the sandwich assay.

In some cases, a competitive assay may be used. In addition to the patient sample, a competitor to the targeted protein is added to the reaction mix. The competitor and the HCC marker protein compete for binding to the specific binding partner. Usually, the competitor molecule will be labeled and detected as previously described, where the amount of competitor binding may be proportional to the amount of target protein present. The concentration of competitor molecule will be from about 10 times the maximum anticipated protein concentration to about equal concentration in order to provide the most sensitive and linear range of detection.

One further type of protocol for generating expression profiles is an array-based antibody binding profile generation protocol.

After the HCC protein profile of the sample has been obtained, the expression profile is compared with a reference or control profile to conduct an evaluation of the subject from which the sample was obtained. In certain embodiments, the comparison is made with a profile from a sample from a control source (which, in certain embodiments, may be from unaffected, normal individuals). In other embodiments, the comparison may be made with a profile from a sample from an individual with cirrhosis and/or hepatitis viral infection. A control dataset may include data that is obtained from a sample that is known to be from a subject having HCC, and therefore may be a positive control profile.

In certain embodiments, the obtained profile is compared to a single control/reference profile to obtain information regarding the phenotype of the subject being assayed. In yet other embodiments, the obtained profile is compared to two or more different reference/control profiles to obtain information regarding the phenotype of the assayed sample. For example, the test profile may be compared to positive and negative reference profiles to obtain a reliable indication that the subject from which the sample was obtained has HCC.

In one embodiment, a difference value, i.e., a numerical evaluation of the difference between a test profile and a control profile may be calculated using any convenient methodology, where a variety of methodologies are known to those of skill in the array art, e.g., by comparing digital images of the expression profiles, by comparing databases of expression data, and the like. Patents describing ways of comparing expression profiles include, but are not limited to, U.S. Pat. Nos. 6,308,170 and 6,228,575, the disclosures of which are herein incorporated by reference.

Samples can be obtained from the tissues or fluids of an individual as well as from cell cultures or tissue homogenates. For example, samples can be obtained from whole blood, tissue biopsy, serum, and the like. Also included in the term are derivatives and fractions of such cells and fluids. Where cells are analyzed, the number of cells in a sample may be at least about $10^2$, usually at least $10^3$, and may be about $10^4$ or more. The cells may be dissociated, in the case of solid tissues, or tissue sections may be analyzed. Alternatively a lysate of the cells may be prepared.

In certain embodiments, the profile of the above-described marker protein or proteins in the sample, e.g., blood serum, is statistically analyzed to provide an evaluation of HCC. In such methods, the profile may be compared to one or more control profiles to provide the evaluation.

The analysis methods may further include input from additional variables, including clinical indicia. Clinical indicia may be assessed and those data may be combined with the marker expression data to provide a diagnosis for HCC. Such clinical markers include, without limitation: red blood cell count, blood sugar, blood calcium, serum cholesterol, etc. Other variables include metabolic measures, genetic information, family history, measures derived from combinations of the above, and other data obtained from a subject.

In certain embodiments, the method may include: a) receiving a sample, b) evaluating the sample according to the above-described methods to produce an evaluation of HCC, e.g., a diagnosis; and c) communicating the evaluation. The sample may be received from a remote location and/or the diagnosis may be communicated to a remote location, where a 'remote location' is meant a second location other than a first location. For example, a remote location could be a different room in the same building (e.g., another laboratory), a different building in the same building complex, or a different location in the same city, state or country, etc. When a cellular sample is indicated as being 'received' from a remote location, the cellular sample may be obtained from the remote location or hand-delivered, mailed or couriered from the remote location, for example. 'Communicating', in this context, refers to any means of getting that information from one location to the next, whether by physically transporting printed material or computer readable media containing the information (e.g., by mail), or by transmitting the information. If information is transmitted, a digital or analog signal representing the information (e.g., a electromagnetic signal such as a light or electrical signal) is transmitted over a suitable communication channel (for example, a private, public or wireless network). Any convenient means may be employed for transmitting the data, e.g., facsimile, modem, internet, e-mail, and the like.

Data Analysis

In order to identify HCC marker protein profiles that are indicative of HCC, a statistical test may be employed. In certain embodiments, the test may provide a confidence level for a change in the markers between the test and control profiles to be considered significant. The raw data may be initially analyzed by measuring the values for each marker, in duplicate, triplicate or in multiple duplicates.

In certain embodiments, a test profile is considered to be different from a normal control profile if at least three of the markers are present at greater than a pre-determined level, i.e., such that the levels exceed the limits that correspond to a predefined level of significance.

In certain embodiments, a test profile is considered to be different from a normal control profile if at least one of the markers selected from the group consisting of: M-CSF, IL8 and MMP10 is present at greater than a pre-determined level, i.e., such that the levels exceed the limits that correspond to a predefined level of significance.

In certain embodiments, a test profile is considered to be different from a normal control profile if at least two of the markers selected from the group consisting of: M-CSF, IL8 and MMP10 are present at greater than a pre-determined level, i.e., such that the levels exceed the limits that correspond to a predefined level of significance.

Data analysis methods suitable for use herein, for example, nearest neighbor classifier, partial-least squares, SVM, AdaBoost and a clustering-based classification methods are described in great detail in a large number of publications including Ben-Dor et al (J. Comput. Biol. 2000 7: 559-83), Nguyen et al (Bioinformatics 2002 18:39-50), Wang et al (BMC Bioinformatics 2003 4:60), Liu et al (Genome Inform. Ser. Workshop Genome Inform. 2001 12:14-23), Yeang et al (Bioinformatics. 2001; 17 Suppl 1:S316-22) and Xiong (Biotechniques. 2000 December; 29(6):1264-8, 1270), and many others.

In certain embodiments, the false discovery rate (FDR) for any statistical score that provides a measurement of how different the profiles between two groups of samples are may be calculated. In one example, the t-test score or TNoM score may be calculated. The TNoM score is described in the Ben-Dor reference cited above.

In one embodiment, to provide significance ordering, the false discovery rate (FDR) may be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001) PNAS 98, 5116-21). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300, 1000, or 10000. Using the N distributions, one calculates an appropriate measure (mean, median, etc.) of the count of correlation coefficient values that their values are equal or exceed the value (of similarity) that is obtained from the distribution of experimentally observed similarity values at a given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental profiles.

In certain embodiments, particularly when the number of samples is small (e.g., less than about 20 or 30), the 'leave one out' cross validation (LOOCV) method may be employed (see Ben-Dor et al (J. Comput. Biol. 2000 7: 559-83)). In this method, at each step of the analysis one or more samples are removed or 'hidden' from the data, and the classifier is built based on the remaining samples. This classifier is applied to the hidden sample or samples to determine class or disease status of these samples. The classifier may be constructed based on the expression profile of each protein independently using probabilistic naïve Bayesian approach. Then these per protein classifiers are combined for a given set of proteins to produce the final classification of the samples. The above procedure is repeated for all samples, and the final number of correct sample classifications is reported. The set of proteins that produces the best success rate is reported as a best predictor set.

Using the aforementioned distribution, a level of confidence may be chosen. This may be used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual 'random correlation' distributions, one can find how many observations fall outside the threshold range. This procedure provides a sequence of counts. The mean and the standard deviation of the sequence provide the average number of potential false positives and its standard deviation.

The data may be subjected to non-supervised hierarchical clustering to reveal relationships among profiles. For example, hierarchical clustering may be performed, where the Pearson correlation is employed as the clustering metric. One approach is to consider a patient HCC dataset as a 'learning sample' in a problem of 'supervised learning'. CART is a standard in applications to medicine (Singer (1999) Recursive Partitioning in the Health Sciences, Springer), which may be modified by transforming any qualitative features to quantitative features; sorting them by attained significance levels, evaluated by sample reuse methods for Hotelling's $T^2$ statistic; and suitable application of the lasso method. Problems in prediction are turned into problems in regression without losing sight of prediction, indeed by making suitable use of the Gini criterion for classification in evaluating the quality of regressions.

This approach has led to what is termed FlexTree (Huang (2004) PNAS 101:10529-10534). FlexTree has performed very well in simulations and when applied to SNP and other forms of data. Software automating Flextree has been developed. Alternatively LARTree or LART may be used. Recent efforts have led to the development of such an approach, termed LARTree (or simply LART) Turnbull (2005) Classification Trees with Subset Analysis Selection by the Lasso, Stanford University. The name reflects binary trees, as in CART and FlexTree; the lasso, as has been noted; and the implementation of the lasso through what is termed LARS by Efron et al. (2004) Annals of Statistics 32:407-451. See, also, Huang et al. (2004) Tree-structured supervised learning and the genetics of hypertension. Proc Natl Acad Sci USA. 101 (29):10529-34.

Other methods of analysis that may be used include logic regression. One method of logic regression is detailed by Ruczinski (2003) Journal of Computational and Graphical Statistics 12:475-512. Logic regression resembles CART in that its classifier can be displayed as a binary tree. It is different in that each node has Boolean statements about features that are more general than the simple 'and' statements produced by CART.

Another approach is that of nearest shrunken centroids (Tibshirani (2002) PNAS. 99:6567-72). The technology is k-means-like, but has the advantage that by shrinking cluster centers, one automatically selects features (as in the lasso) so as to focus attention on small numbers of those that are informative. The approach is available as PAM software and is widely used. Two further sets of algorithms are random forests (Breiman (2001) Machine Learning 45:5-32 and MART (Hastie (2001) The Elements of Statistical Learning, Springer). These two methods are already 'committee methods.' Thus, they involve predictors that 'vote' on outcome.

In another analytical approach, variables chosen in the cross-sectional analysis are separately employed as predictors. Given the specific ASCVD outcome, the random lengths of time each patient will be observed, and selection of proteomic and other features, a parametric approach to analyzing survival may be better than the widely applied semi-parametric Cox model. A Weibull parametric fit of survival permits the hazard rate to be monotonically increasing, decreasing, or constant, and also has a proportional hazards representation (as does the Cox model) and an accelerated failure-time representation. All the standard tools available in obtaining approximate maximum likelihood estimators of regression coefficients and functions of them are available with this model.

In addition the Cox models may be used, especially since reductions of numbers of covariates to manageable size with the lasso will significantly simplify the analysis, allowing the possibility of an entirely nonparametric approach to survival.

These statistical tools are applicable to all manner of proteomic data. A set of biomarker, clinical and genetic data that can be easily determined, and that is highly informative regarding detection of individuals with clinically significant HCC is provided.

Computer-Related Embodiments

Also provided is a computer readable medium containing computer-readable instructions for performing the methods described above, i.e., for comparing an HCC protein marker profile to a control profile to provide an evaluation whether a subject has HCC. Also provided are databases of profiles of HCC marker proteins. Such databases will typically comprise expression profiles of individuals having HCC of varying severity (from mild to severe) and normal individuals, as well as, in certain embodiments, individuals having cirrhosis, where such profiles are as described above. In certain embodiments, the instructions and the database may be employed together to perform the instant methods. In one embodiment, the instructions may contain a list of proteins, control profiles, and software for comparing an experimental profile to one or more of the control profiles.

The programming and database may be implemented in hardware or software, or a combination of both. In one embodiment, a computer-readable storage medium is provided, the medium comprising a data storage material encoded with machine readable data which, when using a machine programmed with instructions for performing the above-described the data to provide an evaluation of HCC. Such data may be used for a variety of purposes, such as patient monitoring, initial diagnosis, and the like. This embodiment may be implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

The subject programming may be implemented in a high level procedural or object oriented programming language to communicate with a computer system. However, the programs can be implemented in assembly or machine language, if desired. In any case, the language may be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

The expression profiles and databases thereof and the programming may be provided in a variety of media to facilitate their use. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. 'Recorded' refers to a process for storing information on computer readable medium, using any such methods as known in the art. Any convenient data storage structure may be chosen, based on the means used to access the stored information. A variety of data processor programs and formats can be used for storage, e.g. word processing text file, database format, and the like.

Mammalian Subjects

The above-described methods may be performed on a mammalian subject, e.g., a human, who is: a) suspected of having HCC, or b) not suspected of having HCC, to determine if that subject has HCC. In certain embodiments, the methods may be performed on a subject who has a liver-disease related symptom, e.g., abdominal pain, an enlarged liver, ascites, jaundice, muscle wasting, hepatitis (e.g., HCV infection), or esophageal varices and the like to determine if that subject has HCC. In one embodiment, the subject is phenotypically normal, e.g., does not show any symptoms of HCC.

In particular embodiments, the subject may have low or normal AFP levels in blood serum and, as such, may be diagnosed as not having HCC using an AFP-based test. In these embodiments, the subject may have an AFP concentration of 0 µg/l (undetectable) to 20 µg/l, e.g., 0 µg/l (undetectable) to 5 µg/l, 5 µg/l to 10 µg/l, 10 µg/l to 15 µg/l, or 15 µg/l to 20 µg/l, in blood serum.

Systems

Also provided is an HCC evaluation system that comprises capture agents, e.g., antibody proteins, that specifically bind to three or more of the above-described markers. The system may be employed to provide a quantitative evaluation of the abundance of proteins in blood serum. In certain embodiments, the capture agents are bound to a substrate, e.g., the wells of a multi-well plate or a surface of a glass slide.

In one embodiment, the capture agents may be arranged in the form of an array. An array can be created by spotting captures agents onto a substrate (e.g., glass, nitrocellulose) and attaching those capture agents to the substrate. The probes can be bound to the substrate by either covalent bonds or by non-specific interactions, such as hydrophobic interactions. Techniques for constructing arrays and methods of using these arrays are described in, for example, Schena et al. (1996) *Proc Natl Acad Sci USA.* 93(20):10614-9; Schena et al. (1995) *Science* 270(5235):467-70; Shalon et al. (1996) *Genome Res.* 6(7):639-45, U.S. Pat. No. 5,807,522, EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734.

The probes utilized in the arrays can be of varying types and can include, for example, antibodies, including antibody fragments, aptamers, avimers, or peptidomimetics.

Common physical substrates for making protein arrays include glass or silicon slides, magnetic particles or other micro beads, functionalized with aldehyde or other chemical groups to help immobilize proteins. The substrate can also be coated with PLL, nitrocellulose, PVDF membranes or modified with specific chemical reagents to adsorb capture agents. The desirable properties of an ideal surface include: chemical stability before, during, and after the coupling procedure, suitability for a wide range of capture agents (e.g., hydrophilic and hydrophobic, low MW and high MW), minimal non-specific binding, low or no intrinsic background in detection, presentation of the capture agents in a fully-functional orientation, production of spots with predictable and regular morphology (shape, signal uniformity).

The variables in the immobilization of proteins include: type of capture agent, nature of surface (including any pretreatment prior to use), and the immobilization method. Both adsorption and covalent attachment have been used for protein arrays. Orientation of the capture agent is very important in presenting it to the ligand or the surface in a functional state. Although covalent attachment using a variety of chemically activated surfaces (e.g., aldehyde, amino, epoxy) as well as attachment by specific biomolecular interactions (e.g., biotin-streptavidin) provide a stable linkage and good reproducibility, chemical derivatization of the surface may alter the biological activity of the capture agent and/or may result in multi-site attachment.

In one embodiment, antibody arrays are made with a non-contact deposition printer. The printer uses thermal ink jet heads that can print many solutions simultaneously to produce hundreds of spots of 50-60 μm diameter with a spacing of 150 μm between spots. The droplet volume ranges between 35 pL to 1.5 mL. The heating element is made out of TaAl or other suitable materials, and is capable of achieving temperatures that can vaporize a sufficient volume of printing buffer to produce a bubble that will push out a precise volume of the antibody solution on the substrate. Selection of printing buffer is important, in that the buffer accomplishes the following: increases printing efficiency (measure of the number of spots that are printed to the total number of spots that are attempted), reduces sample spreading, promotes uniform delivery, stabilizes the capture agents that are being printed, reduces sample drying, increases the visibility of the printed spots. In addition to the printing buffer, other variables that affect printing include: size of the drops, the method of washing and drying the print head, and the speed at which the dispensing head moves. Various modifications may be within these conditions.

Both direct labeling and sandwich format approaches may find use. In the direct labeling procedure, the antibody array is interrogated with serum samples that have been derivatized with a fluorescent label, e.g. Cy3, Cy5 dye. In the sandwich assay procedure, unlabeled serum is first incubated with the array to allow target proteins to be captured by immobilized capture antibodies. Next, the captured target proteins are detected by the application of a labeled detection antibody. The sandwich assay provides extra specificity and sensitivity needed to detect pg/mL concentrations of cytokines, without compromising the binding affinities of the target protein through a direct labeling procedure.

Fluorescence intensity can be determined by, for example, a scanning confocal microscope in photon counting mode. Appropriate scanning devices are described by e.g., U.S. Pat. No. 5,578,832 to Trulson et al., and U.S. Pat. No. 5,631,734 to Stern et al. and are available from Affymetrix, Inc., under the GeneChip™ label or from other manufacturers such as Agilent Technologies, Inc. Some types of label provide a signal that can be amplified by enzymatic methods (see Broude, et al., Proc. Natl. Acad. Sci. U.S.A. 91, 3072-3076 (1994)). A variety of other labels are also suitable including, for example, radioisotopes, chromophores, magnetic particles and electron dense particles.

Those locations on the probe array that are bound to a sample are detected using a reader, such as described by U.S. Pat. No. 5,143,854, WO 90/15070, and U.S. Pat. No. 5,578, 832. For customized arrays, the hybridization pattern can then be analyzed to determine the presence and/or relative amounts or absolute amounts of known species in samples being analyzed as described in e.g., WO 97/10365.

Other methodologies also find use. In some embodiments, a solution based methodology utilizes capillary electrophoresis (CE) and microfluidic CE platforms for detecting and quantitating protein-protein interactions. This technique can be performed easily by any laboratory with access to a standard CE DNA sequencing apparatus. With this methodology, a fluorescent marker (eTag reporter) is targeted to the analyte with one antibody, and a second sandwich antibody of a different epitope specificity that is chemically coupled to a 'molecular scissors' induces release of the fluorescent probe when both antibodies are in close apposition on the specific analyte. Quantitation then is focused on the liberated eTag, that is quantified with a standard DNA capillary sequencing device. The eTag Assay System can be used to measure the abundance of multiple proteins simultaneously. A critical feature of the assay is that the affinity agents (antibodies) are not immobilized on surfaces, as is required with array technologies. Solution-based binding eliminates surface-induced denaturation and non-specific binding, and improves sensitivity and reaction kinetics.

By combining different colors in the eTag reporters, both mobility and color may be used to dramatically increase the degree of multiplexing. Many binding reactions can be multiplexed in the same vessel, followed by CE to identify the released eTag reporters. Each released eTag reporter encodes the identity of the probe to which it was originally attached. As a result, it is straightforward to configure multiplexed assays to monitor various types of molecular recognition events, especially protein-protein binding.

Kits

Finally, kits for use in practicing the subject invention are also provided. The subject kits at least include an HCC evaluation system discussed above. For example, certain embodiments of the subject invention include kits that have a plurality of capture agents for HCC marker proteins attached to the surface of a solid support. A kit may comprise the computer-readable medium described above.

The kits may further include one or more additional components necessary for carrying out a binding assay, such as binding buffers, and the like. As such, the kits may include one or more containers such as vials or bottles, with each container containing a separate component for the assay, and reagents for carrying out an array assay such as a nucleic acid hybridization assay or the like. The kits may also include a reagent for preparing the sample, and a syringe for drawing blood from a subject, as well as suitable negative and positive controls.

In addition to a system, a subject kit may also include written instructions for use in the above-described method. The instructions may be printed on a substrate, such as paper or plastic. As such, the instructions may be present in the kits as a package insert, in the labeling of the container of the kit or components thereof (i.e., associated with the packaging or sub-packaging). In other embodiments, the instructions are present as an electronic storage data file present on a suitable computer readable storage medium, e.g., CD-ROM, diskette, etc. The instructions may include software or algorithms for data visualization or data analysis as described above. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

The subject kit may also include a computer-readable medium containing the above-described instructions, or means for accessing such instructions such as means for obtaining the algorithms from a remote source, e.g. via the Internet.

In many embodiments of the subject kits, the components of the kit are packaged in a kit containment element to make a single, easily handled unit, where the kit containment element, e.g., box or analogous structure, may or may not be an airtight container, e.g., to further preserve the one or more biopolymeric arrays and reagents, if present, until use.

Utility

In general terms, the above-described methods may be employed to evaluate a subject for HCC, e.g., diagnose or monitor HCC or (qualitatively or quantitatively) assess the degree of HCC of a subject. In certain embodiments, the subject methods may be performed to provide a diagnosis of HCC, or an indication that the subject is normal (i.e., does not have HCC). The methods may be employed to distinguish between individuals having cirrhosis and individuals having HCC.

In other embodiments, the methods may be employed to determine how severely a patient is affected by HCC. For example, depending on the similarity or difference of the profile to positive or negative controls, the subject may be evaluated as having mild HCC, intermediate HCC, or severe HCC. Further, based on the continuum of values that are obtained for a population of subjects having HCC, a test subject's HCC may be categorized (in some cases, arbitrarily) into a group that describes the severity of HCC. The method may be employed to diagnose early stage HCC, and allow magnetic resonance imaging (MRI) testing to be avoided.

In certain embodiments, a subject may be tested several times in a time period, e.g., a year, to determine whether there is a change in the pattern of expression of the one, two, three or more HCC-associated serum proteins. An increase in expression over time can indicate that the individual is developing HCC. As with other measures, the dataset for the patient may be compared to a control dataset. The baseline in such analyses can be a prior value determined for the same individual or a statistical value (e.g., mean or average) determined for a control group (e.g., a population of individuals with no apparent risk factors). An individual showing a statistically significant increase in HCC-associated protein expression levels over time can prompt the individual's physician to take prophylactic measures to lessen the individual's potential for developing severe HCC. For example, the physician can recommend certain life-style changes (e.g., medication, improved diet, exercise program), surgery, or a liver transplant, to reduce the risk of developing severe HCC. In order to confirm a diagnosis of HCC, the physician may also perform other tests, e.g., an AFP-based test, an ultrasound, a computerized axial tomography (CT scan) or magnetic resonance imaging (MRI) examination.

EXAMPLES

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

General Protocol for Array Processing

The antibody array was manufactured using Agilent Technologies, Inc. in-house thermal ink-jet deposition system. Eight identical arrays were on 1×3 inch slide. The surface of antibody arrays was blocked with 6-12% non-fat milk for 10 minutes at room temperature in a staining dish (Aldrich Z10, 396-9) under constant shaking. The slide was washed twice with 10 mM phosphate saline buffer (pH 7.4) containing 0.05% Tween 20 for about 3-5 minutes, then washed once with 10 mM phosphate buffer (pH 7.4) for 3 minutes before briefly rinsing with de-ionized water. The slide was then spun dry by centrifuge at 1500 rpm (Beckman GPKR).

The plasma samples from patients and healthy controls were diluted 1:3 in 1% casein block (Pierce 37528) containing 0.6% Triton X-100. 40 uL of the above solution was applied onto 8-pack gasket slide (Agilent G2534-60007) and the slide was assembled using Agilent Surehyb gasket chamber (Agilent G2534A). Each sample was assayed at least twice on different slide. The incubation was carried out at room temperature overnight in a hybridization incubator (Robbins Scientific, Model 400). The slide was washed twice with 10 mM phosphate saline buffer (pH 7.4) containing 0.05% Tween 20 for 10 minutes and once with 10 mM phosphate buffer (pH 7.4) for 10 minutes before briefly rinsing with de-ionized water. The slide was then spun dry by centrifuge at 800×g for 2 minutes.

The biotinylated secondary antibodies were dissolved in 1% casein block (Pierce, 37528) containing 0.4% Triton X-100 at recommend concentrations by manufacturer. 40 uL of biotinylated antibodies was applied onto 8-pack gasket slide. The incubation lasted 2.5 hours at room temperature in a hybridization incubator (Robbins Scientific, Model 400). The slide was washed twice with 10 mM phosphate saline buffer (pH 7.4) containing 0.05% Tween 20 for 10 minutes and once with 10 mM phosphate buffer (pH 7.4) for 10 minutes before briefly rinsing with de-ionized water. The slide was then spun dry by centrifuge at 800×g for 2 minutes.

Cy3-Streptavidin (Sigma P-7949) was diluted 1:2500 in 1% casein block (Pierce 37528) containing 0.4% Triton X-100. 40 ul of Cy3-Streptavidin binding solution was applied onto 8-pack gasket slide. The array was incubated at room temperature for 30 minutes in a hybridization incubator (Robbins Scientific, Model 400). The slide was washed twice with 10 mM phosphate saline buffer (pH 7.4) containing 0.05% Tween 20 for 10 minutes and once with 10 mM phosphate buffer (pH 7.4) for 10 minutes before briefly rinsing with de-ionized water. The slide was then spun dry by centrifuge at 1500 rpm.

The slide was scanned using Agilent Scanner (G2565BA) at 5 um resolution at different PMT settings if pixels were saturated at the highest sensitivity. The array fluorescence data was obtained by Agilent Feature Extraction software, v. 7.5.

Before statistical analysis of the extracted data, several steps of data processing were applied to assess the quality of the data and to reduce noise. Typically, potentially redundant data were collected at four features on one array, at two different printed concentrations of capture antibody, and often, on duplicate arrays which were run on separate slides. Furthermore, the dynamic range of the array was extended by scanning at several PMT settings (e.g., PMT voltages of 5%, 20%, and 100%). In order to simplify the data analysis the redundant data were combined; these steps are not essential but they ease the later analysis. Different combinations of these methods, or different data processing steps could be used according to the data analysis needs. Typical steps of the data processing were:

A. Rejection of outliers from the group of four printed spots;
B. Combination of data from the different PMT settings, scaling the different settings to equal the 100% data, and selecting the data from the linear range of the detector;
C. calculation of the median value from the four printed spots;
D. calculation of an average blank value for each protein, and subtraction of that value from the median value for each protein;
E. combination of duplicates: If both duplicate arrays have usable data, the median data are averaged; otherwise medians from the array with more complete data are used;
F. select data from the concentration of each capture antibody which resulted in more complete data for that protein;
G. log-transform the data (base-10).

Example 2

Detection of Subjects Having Hepatocellular Carcinoma

Antibody Array Composition

Antibodies against the following target antigens are printed at 500 ug/ml and 250 ug/ml. About 60 antibodies were tested. Each antibody is printed 4 replicates per array and per condition.

Sample Selection

The plasma samples were obtained from the Asian Liver Center at Stanford Medical School. Plasma samples from 54 HCC patients, 18 patients with hepatitis or cirrhosis, and 17 normal control subjects were collected for analysis.

Sample Processing

All plasma samples are processed by the protocol as described in Example 1. Each sample is processed twice on different slides. The samples are arranged in a way that each slide contains samples from different categories. The array measurements were highly reproducible; median values from duplicate arrays typically had an $r^2$ value=0.99, while median values from different samples typically resulted in $r^2$ values of 0.96 or less.

Data Processing

The array data is processed based on the protocol as outlined in Example 1. The goal of the data processing was simply to provide one list of background subtracted values, corresponding to protein levels, for each patient or sample. The resulting combined table of (samples)×(protein levels) could then be readily analyzed using statistical tools. Several steps of the data processing (such as combination of duplicate arrays) provided a measure of quality of the experiment or sample, such that aberrant samples/arrays/slides or proteins could be removed from the dataset before the final analysis. The original data were retained such that different methods of data processing could be applied to the same experimental data in the future.

Data Analysis and Protein Marker Profile Determination

Figure 2B:
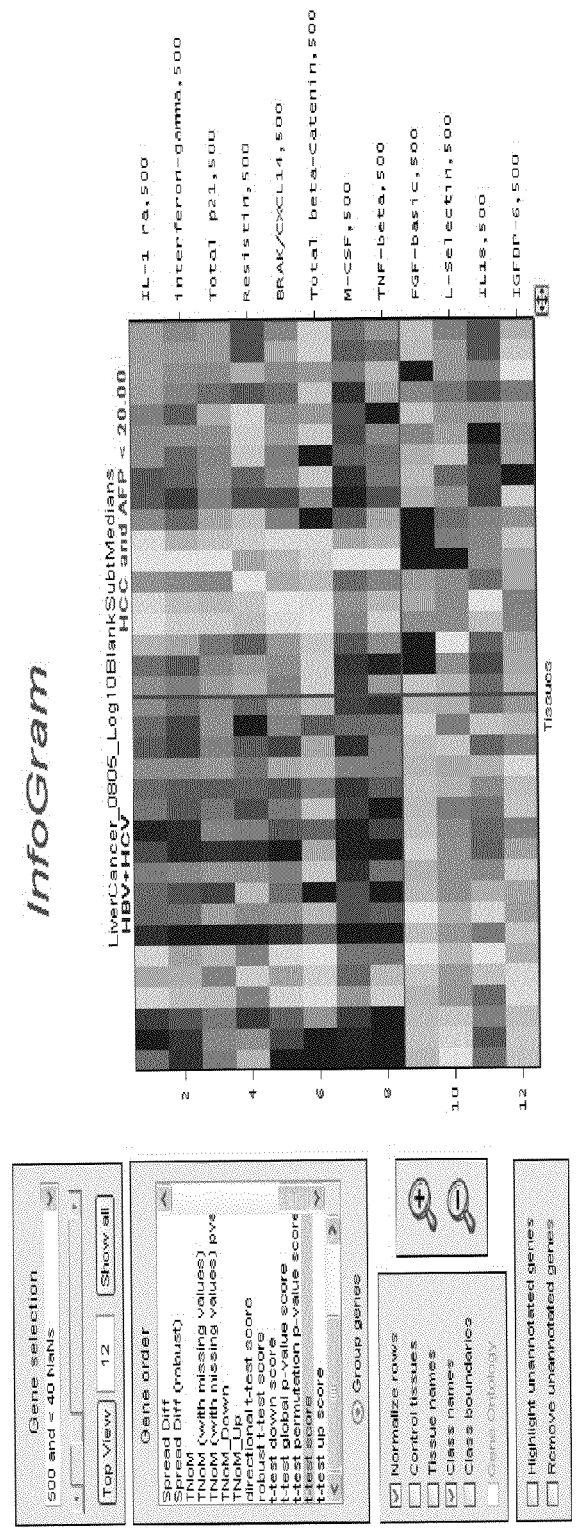
Figure 3B:
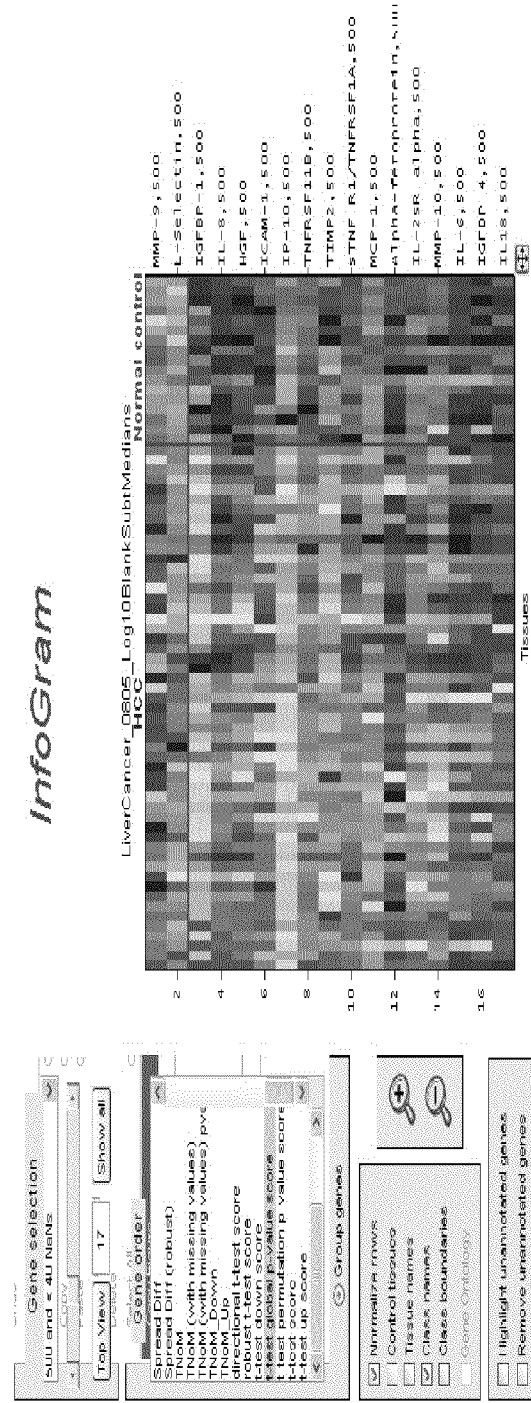

Data analysis included several steps. At first, we identified proteins that have statistically significant differential expression between two or more groups of samples—we used ANOVA, Student t-test, and TNoM score (described in Ben-Dor et al (J. Comput. Biol. 2000 7: 559-83)), many other scoring methods can be applied to such data. Examples of actual score for several proteins are shown in FIGS. 1A, 2A and 3A. The differential protein expression for the patients in two groups is also represented by the heatmaps of FIGS. 1B, 2B and 3B. The lighter shade represents higher expression of the protein and darker-shade represents the lower expression of the proteins.

In addition to evaluating differential expression for each protein independently, we used leave one out cross validation analysis to identify sets of proteins that together can predict disease status of the patient.

Statistical analysis showed that HCC patients and cirrhosis patients (patients having hepatitis infection by HCV and HBV) could be distinguished by evaluating more than one of: total beta-Catenin, M-CSF, Total p21, IL-1 ra, Resistin, L-Selectin, IGFBP-6, IL-6sR, VCAM-1, FGF-basic and Fractalkine/CX3CL1. Representative data are shown in FIGS. 1A and 1B.

Statistical analysis showed that HCC patients having AFP levels below 20 µg/l and cirrhosis patients (patients having hepatitis infection caused by HCV and HBV) could be distinguished by evaluating more than one of: IL-1 ra, interferon-gamma, Total p21, Resistin, BRAK/CXCL14, Total beta-Catenin, M-CSF, TNF-beta, FGF-basic, L-Selectin, IL18, and IGFBP-6. Representative data are shown in FIGS. 2A and 2B.

Statistical analysis showed that HCC patients and normal patients (patients with no clinically significant symptoms of HCC) could be distinguished by evaluating more than one of IGFBP-1, IL-8, HGF, ICAM-1, IP-10, TNFRSF11B, TIMP2, sTNF R1/TNFRSF1A, MCP-1, IL-2sR alpha, MMP-10, IL-6, IGFBP-4, IL18, MMP-9 and L-Selectin. Representative data are shown in FIGS. 3A and 3B.

In addition to the above proteins, alpha-fetoprotein levels may also be assessed.

Example 3

Evaluation of M-CSF as Standalone or Complementary Protein Marker to AFP in HCC Patients in Comparison to Patients with Chronic HBV Infection or Metastatic Liver Cancer Study Outline A total of 187 adults were prospectively enrolled in this study. Serum samples were kept at −80° C. after collection and thawed immediately before the determination of M-CSF levels using an enzyme-linked immunosorbent assay (ELISA) kit according to the manufacturers' instructions (DuoSet, R&D Systems, Inc., Minneapolis, Minn., USA).

Data Analysis and Conclusion

Mean log M-CSF levels were statistically significantly higher in HCC patients than in chronic hepatitis B or liver metastasis patients (Table 1). There were no major discrepancies in the patterns of M-CSF levels between adults aged less than 50 years and those aged 50 years and over; between males and females; or between Asians/Pacific Islanders and non-Hispanic Whites (data not shown). We examined mean log M-CSF levels among subgroups of HCC patients classified by HBV or HCV seropositivity, AFP level, vascular invasion, and tumor size. M-CSF levels were higher in HCV-positive HCC patients than in HBV-positive patients (Table 1), but they were significantly higher in both of these groups than in chronic HBV carriers. Also, they were higher in HCV-positive HCC patients than in metastatic liver cancer patients. HCC patients with AFP levels ≧200 ng/ml had the highest M-CSF levels. Regardless of AFP levels, all HCC patients had significantly higher M-CSF levels than chronic HBV carriers. Higher M-CSF levels were found in patients with tumor vascular invasion than in those without, whereas there was no difference in M-CSF level by tumor size.

| HCC patient subgroup | HCC Mean | HBV infection Mean | HBV infection P-value | Liver metastasis Mean | Liver metastasis P-value |
|---|---|---|---|---|---|
| All HCC | 678.58 | 441.42 | <0.001 | 512.86 | 0.02 |
| HBV or HCV seropositivity | | | | | |
| HBV-positive | 607.89 | | 0.006 | | 0.19 |
| HCV-positive | 906.87 | | <0.001 | | 0.001 |
| Tumor vascular invasion | | | | | |
| No | 607.89 | | 0.003 | | 0.17 |
| Yes | 788.40 | | <0.001 | | 0.01 |
| Tumor diameter (cm) | | | | | |
| <5 | 706.27 | | 0.002 | | 0.02 |
| ≧5 | 720.54 | | 0.005 | | 0.06 |
| Alpha-fetoprotein level (ng/ml) | | | | | |
| <20 | 626.41 | | 0.006 | | 0.15 |
| 20-199 | 639.06 | | 0.02 | | 0.20 |
| ≧200 | 788.39 | | <0.001 | | 0.01 |

Table 1 shows the unadjusted differences in M-CSF levels (pg/ml) between HCC patients and control groups, including patients with chronic HBV infection or metastatic liver cancer.

Statistical analysis showed that HCC patients and patients with chronic HBV infection or metastatic liver tumors could be distinguished by evaluating M-CSF levels, with or without the additional measurement of alpha-fetoprotein levels. Representative data are shown in Table 1 {Sun H et al. (2008), Biomarker Insights 3, pp. 1-18; Yan X et al. (2008), American Association for Cancer Research 99th Annual Meeting, San Diego}.

Example 4

Evaluation of MMP-10 and IL-8 as Standalone Protein Markers in HBV-Associated HCC Patients in Comparison to HBV Carriers without HCC Study Outline A total of 50 patients were prospectively enrolled in this study. Serum samples were kept at −80° C. after collection and thawed immediately before the determination of MMP-10 and IL-8 levels using enzyme-linked immunosorbent assay (ELISA) kits according to the manufacturers' instructions (DuoSet, R&D Systems, Inc., Minneapolis, Minn., USA).

Data Analysis and Conclusion

Both MMP-10 and IL-8 levels were significantly higher in HCC patients than in HBV carriers (Student's t-test, $p<0.001$). For IL-8, two extreme outliers were removed from the analysis.

Statistical analysis showed that HBV-associated HCC patients and HBV carriers (without HCC) could be distinguished by evaluating IL-8 levels or MMP-10 levels. Representative data are shown in Table 2.

| Variables | Carrier (n = 24) | HCC (n = 26) | P value |
|---|---|---|---|
| Age | 45.9 ± 13.4 | 61.3 ± 11.6 | <0.001 |
| Sex (M/F) | 14/10 | 21/5 | 0.124 |
| MMP-10 (pg/mL) | 583.6 ± 243.4 | 944.1 ± 589.9 | 0.008 |
| TIMP-2 (ng/mL) | 69.1 ± 13.0 | 79.1 ± 24.8 | 0.083 |
| IL-8 (pg/mL) | 120.6 ± 487.8 | 43.1 ± 56.7 | 0.425 |
| IL-8 (pg/mL) corrected for outliers | 2.4 ± 4.4 (n = 22) | 43.1 ± 56.7 | 0.002 |
| MMP-10 (pg/mL)>600 | 9/15 | 18/8 | 0.046 |
| IL-8 (pg/mL) >10 | 3/21 | 16/10 | <0.001 |

Table 2 shows the unadjusted differences in MMP-10 (pg/ml) and IL-8 (pg/ml) levels between HCC patients and patients with chronic HBV infection.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of distinguishing hepatocellular carcinoma (HCC) from viral induced cirrhosis in a subject, comprising:
    a) measuring levels of at least three HCC markers selected from one or both of a first group (i) and a second group (ii) of markers in a biological sample from said subject to obtain a hepatocellular carcinoma marker profile from said subject;
    b) comparing said marker profile to a control profile obtained from a viral-induced cirrhosis control sample, wherein differential expression of the at least three HCC markers in said biological sample compared to the control sample indicates a diagnosis of hepatocellular carcinoma in said subject; and wherein
    c) said differential expression comprises decreased expression in said first group of HCC markers and increased expression in said second group of HCC markers, and wherein
    d) said first group (i) consists of L-Selectin, IGFBP-6, IL-6sR, VCAM-1, FGF-basic, Fractalkine/CX3CL1, IL18; and
    e) said second group (ii) consists of β-Catenin, M-CSF, IL-8, MMP-10, Total p21, IL-1 ra, Resistin, interferon-gamma, BRAK/CXCL14, TNF-beta.

2. A method of distinguishing hepatocellular carcinoma (HCC) from viral induced cirrhosis in a subject, comprising:
    a) measuring levels of at least one HCC marker selected from the group consisting of M-CSF and MMP-10 in a biological sample from said subject to obtain a hepatocellular carcinoma marker profile from said subject;

b) comparing said marker profile to a control profile obtained from a viral-induced cirrhosis control sample, wherein increased expression of the at least one HCC marker in said biological sample compared to the control profile indicates a diagnosis of hepatocellular carcinoma in said subject.

3. The method according to one of claim 1 or 2, wherein said sample is whole blood, blood serum or blood plasma.

4. The method according to one of claim 1 or 2, wherein said obtaining a hepatocellular carcinoma marker profile comprises:
contacting said sample with capture agents that specifically bind to hepatocellular carcinoma protein markers;
detecting binding of proteins in said sample to said capture agents;
wherein an alteration in said binding, compared to a control sample, is indicative of hepatocellular carcinoma.

5. The method according to one of claim 1 or 2, wherein said sample is contacted with a panel of capture agents that specifically bind to said hepatocellular carcinoma protein markers.

6. The method according to one of claim 1 or 2, furthermore assessing clinical indicia.

7. The method according to claim 6, wherein said clinical indicia comprise symptoms of HCC.

8. The method according to claim 1, wherein said method is combined with an alpha-fetoprotein (AFP) blood test to provide a diagnosis of HCC.

9. A method comprising:
a) receiving a sample;
b) evaluating said sample according to the method of one of claim 1 or 2 to produce an indication of hepatocellular carcinoma (HCC) of a subject; and
c) communicating said results.

10. The method of claim 9, wherein said sample is received from a remote location.

11. The method of claim 9, wherein said sample is communicated to a remote location.

12. The method according to claim 1, wherein comparing hepatocellular carcinoma marker profiles comprises use of a computer readable medium comprising instructions for comparing a hepatocellular carcinoma marker profile to a control profile to provide a diagnosis of HCC.

13. The method according to claim 1, wherein said subject has alpha-fetoprotein serum levels of less than 20 µg/l.

14. The method according to one of claim 1 or 2, wherein said method furthermore provides an indication of disease progression.

15. The method according to claim 2, wherein said subject has alpha-fetoprotein serum levels of less than 20 µg/l.

* * * * *